US00PP34127P2

(12) United States Plant Patent
Kamstra

(10) Patent No.: US PP34,127 P2
(45) Date of Patent: Apr. 12, 2022

(54) POINSETTIA PLANT NAMED 'EURZ0023'

(50) Latin Name: *Euphorbia pulcherrima*
Varietal Denomination: EURZ0023

(71) Applicant: SYNGENTA CROP PROTECTION AG, Basel (CH)

(72) Inventor: Silvan Adelmar Kamstra, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/158,160

(22) Filed: Jan. 26, 2021

(51) Int. Cl.
*A01H 5/12* (2018.01)
*A01H 6/38* (2018.01)

(52) U.S. Cl.
USPC ..... Plt./306

(58) Field of Classification Search
USPC ..... Plt./302, 303, 306
See application file for complete search history.

*Primary Examiner* — Susan McCormick Ewoldt
(74) *Attorney, Agent, or Firm* — Dale Skalla

(57) ABSTRACT

A new *Poinsettia* plant named 'EURZ0023' particularly distinguished by the distinct hot pink color, dark green foliage, and compact vigor with very good branching and strong stems.

1 Drawing Sheet

Latin name of the genus and species of the plant claimed: *Euphorbia pulcherrima.*

Varietal denomination: 'EURZ0023'.

BACKGROUND OF THE NEW PLANT

The present invention comprises a new *Poinsettia*, botanically known as *Euphorbia pulcherrima*, and hereinafter referred to by the variety name 'EURZ0023'.

'EURZ0023' is a product of a designed crossing between a plant called '22866', the female parent, not patented, and 's90-1520-01', the male parent, not patented. '22866' has red bracts and is smaller than 'EURZ0023'. 's90-1520-01' has the same bract color as 'EURZ0023', however, the bract size is bigger and the leaves are more dented. The new cultivar has hot pink bract color. The variety has medium size inflorescences with bracts a little upright directed, dark green foliage, and compact vigor with good branching.

'EURZ0023' originates from cross made in 2012 in Enkhuizen, The Netherlands.

A greenhouse crop was developed from the first selected plant and evaluated. These plants were multiplied separately and examined during next fall-winter flowering for uniformity and stability of the new combination of characteristics.

BRIEF SUMMARY OF INVENTION

Horticultural examination of plants grown from cuttings of the plant initiated in April 2015, and continuing thereafter, has demonstrated that the combination of characteristics as herein disclosed for 'EURZ0023' are firmly fixed and are retained through successive generations of asexual reproduction in Enkhuizen, The Netherlands.

'EURZ0023' has not been observed under all possible environmental conditions. The phenotype may vary significantly with variations in environment such as temperature, light intensity and day length.

A Plant Breeder's Right for this cultivar has not been applied for. 'EURZ0023' has not been made publicly available prior to the effective filing date of this application, notwithstanding any disclosure that may have been made less than one year prior to the effective filing date of this application by the inventor or another who obtained 'EURZ0023' directly from the inventor.

The following traits have been repeatedly observed and are determined to be basic characteristics of the new variety. The combination of these characteristics distinguishes this *Poinsettia* as a new and distinct variety.

BRIEF DESCRIPTION OF THE PHOTOGRAPHS

The accompanying photographic drawing shows typical flower and foliage characteristics of 'EURZ0023' with colors being as true as possible with an illustration of this type. The photographic drawings show flowering potted plants of the new variety.

Figure 1:
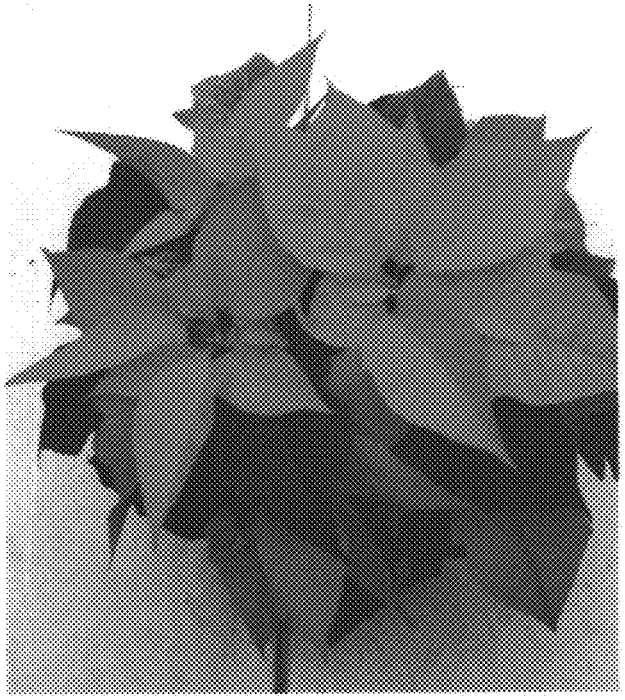

FIG. 1 was taken on Nov. 26, 2020 and shows a view of the bracts from the top of plant, on a plant about 20 weeks old.

Figure 2:
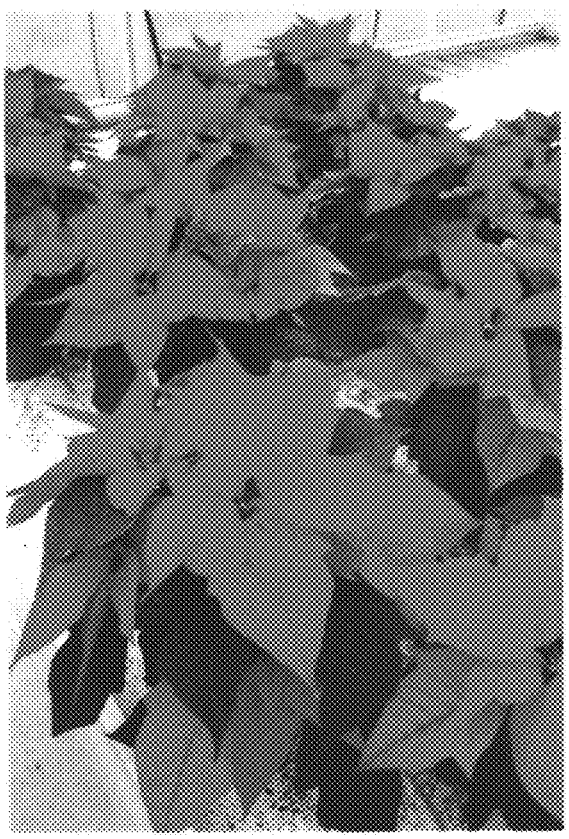

FIG. 2 was taken on Nov. 26, 2020 and shows a group of plants of 'EURZ0023'.

DETAILED BOTANICAL DESCRIPTION

The measurements were taken in Enkhuizen, The Netherlands in December 2020 on 21 weeks old plants growing in a greenhouse. Culture of these plants had started in late June 2020 with planting rooted cuttings in 13 cm pots and terminal pinching about 2 weeks later. The plants were grown under natural day light in the fall (no black cloth to initiate earlier flowering) and at the moderately warm temperature of 18°-20° C. for the bench heating. No use of PGR.

Color references are made to The Royal Horticultural Society Colour Chart (R.H.S.) 2001.

TABLE 1

DIFFERENCES BETWEEN THE NEW VARIETY 'EURZ0023' AND A SIMILAR VARIETY

| | 'EURZ0023' | 'EURZ0003' (U.S. Plant Pat. No. 29,269) |
|---|---|---|
| Plant height: | 20-25 cm | 30-35 cm |
| Cyathia size: | Absent | 0.5 cm |
| Bract color: | RHS 66A | RHS 57C |

Plant:

*Form, growth and habit.*—Shrub, with the branches slanting upright, good branching.

*Plant height* (*inflorescence included*).—20-25 cm.

*Plant width.*—25-30 cm.

Roots:

*Number of days to initiate roots.*—18-20 days at about 24 degrees C.

*Number of days to produce a rooted cutting.*—24-26 days at 24 degrees C.

*Type.*—Fine, fibrous, free branching.

*Color.*—RHS N155C.

Foliage:

*Arrangement.*—Alternate, 8-9 leaves per branch.

*Immature, leaf color, upper surface.*—Approximately RHS 139A.

*Lower surface.*—RHS 147A.

*Mature, leaf color, upper surface.*—RHS 139A.

*Lower surface.*—RHS 147A.

*Venation pattern of the leaf.*—Pinnate.

*Length.*—9-12 cm.

*Width.*—6-10 cm.

*Shape.*—Ovate, with some lobes.

*Base shape.*—Obtuse to rounded.

*Apex shape.*—Acuminate.

*Margin.*—Entire; lobes, mostly rounded some acute.

*Aspect.*—Leaf blades are slightly downwards directed.

*Texture, upper surface.*—Smooth.

*Lower surface.*—Smooth, apart from the protruding veins.

*Color of veins, upper surface.*—RHS 147B and very light RHS 183D for the central vein at base, turning to RHS 147B towards the leaf tip.

*Color of veins, lower surface.*—Central vein RHS 183D turning to RHS 147A towards the leaf tip.

*Petiole color, upper surface.*—RHS 187B.

*Lower surface.*—RHS 184A.

*Length.*—4-5 cm.

*Diameter.*—0.30 cm.

*Aspect.*—Slightly upward directed.

*Texture.*—Glabrous.

Stem:

*Quantity of main branches per plant.*—About 6 to 8.

*Color of stem.*—RHS 147B with slightly RHS 183B.

*Length of stem.*—15-18 cm.

*Diameter.*—0.6-0.8 cm.

*Length of internodes.*—1.0-1.5 cm.

*Texture.*—Glabrous.

*Color of peduncle.*—RHS 144B to RHS 144C.

*Length of peduncle.*—0.2-0.3 cm.

*Peduncle diameter.*—0.2 cm.

*Texture.*—Glabrous.

Inflorescence:

*Type.*—Terminal cyme with surrounding whorl of colored bracts.

*Flowering, commercially* (*sufficiently colored bracts*) .—Mid November.

*Flowering response time.*—About 7.5-8 weeks from equinox.

*Duration of flowering.*—Depends on light and environment, at least 4-6 weeks of shelf life.

*Fragrance.*—Absent.

*Shape of inflorescence.*—Rosette-like whorl, star-shaped; bracts borne nearly horizontally to weakly funnel-shaped (slanting upright); tight center.

*Diameter of inflorescence.*—25 cm.

*Inflorescence, vertical diameter.*—8 cm.

*Number of completely colored bracts per inflorescence* (*sized over 2 cm*).—7-9.

*Single bract, shape.*—Ovate with relatively long, pointed tips, with some weak lobes.

*Bract, apex.*—Acuminate.

*Bract, base.*—Weakly rounded.

*Venation pattern of the bract.*—Pinnate.

*Single bract, length of blade.*—Up to 10 cm, younger bracts diminishing in size.

*Single bract, width of blade.*—Up to 6 cm, younger bract diminishing in size.

*Bract color, upper side.*—RHS 66A.

*Bract color, lower side.*—RHS 71C.

*Vein color, upper surface.*—RHS 66A.

*Vein color, lower surface.*—Approximately RHS 66A.

*Texture.*—Weakly rugose, glabrous.

*Bract petiole color, upper surface.*—RHS 185A.

*Bract petiole color, lower surface.*—RHS 187B.

*Bract petiole, length.*—About 2 cm, shorter with younger bracts.

*Bract petiole diameter.*—0.2-0.3 cm.

Cyme (true inflorescence):

*Cyme, diameter.*—0.5-1.0 cm.

*Number of cyathia.*—Absent or very minor.

*Nectar cups.*—Absent.

Reproductive organs:

*Stamen* (*actually reduced male florets*).—None.

*Shape.*—

*Filament length.*—

*Filament color.*—

*Anther color.*—

*Anther diameter.*—

*Pollen quantity.*—

*Pollen color.*—

*Female flowers.*—

*Fertility/seed set.*—Has not been observed on this plant.

Disease/pest resistance: Disease/pest resistance has not been observed on this plant.

What is claimed is:

1. A new and distinct variety of *Poinsettia* plant named 'EURZ0023,' substantially as illustrated and described herein.

* * * * *